United States Patent [19]

Everly et al.

[11] Patent Number: 4,463,187
[45] Date of Patent: Jul. 31, 1984

[54] PROCESS FOR THE PREPARATION OF 3,5-DIHYDROCARBYL-4-HYDROXYBENZYLMALONIC ACID ESTERS

[75] Inventors: Charles R. Everly; Jerry M. Roper, both of Baton Rouge, La.

[73] Assignee: Ethyl Corporation, Richmond, Va.

[21] Appl. No.: 418,576

[22] Filed: Sep. 15, 1982

[51] Int. Cl.³ .............................................. C07C 67/03
[52] U.S. Cl. ........................................ 560/82; 560/96
[58] Field of Search ..................................... 560/82, 96

[56] References Cited
U.S. PATENT DOCUMENTS 1,984,283  12/1934  Reid et al. ..................... 562/82 X
2,161,213  6/1939  Whitmore et al. ............... 562/82 X

FOREIGN PATENT DOCUMENTS 61183   9/1913  Austria .
653319  5/1951  United Kingdom .

Primary Examiner—Natalie Trousof
Assistant Examiner—Vera C. Clarke
Attorney, Agent, or Firm—Donald L. Johnson; John F. Sieberth; Willard G. Montgomery

[57] ABSTRACT

Esters of 3,5-dihydrocarbyl-4-hydroxybenzylmalonic acid are prepared by reacting a 2,6-dihydrocarbyl-4-halomethylphenol with an ester of a 1,3-dicarboxylic acid in the presence of an alkali or an alkaline earth metal hydride. The products are useful as antioxidants.

17 Claims, No Drawings

PROCESS FOR THE PREPARATION OF 3,5-DIHYDROCARBYL-4-HYDROXYBENZYLMALONIC ACID ESTERS

CROSS-REFERENCE TO RELATED APPLICATIONS

This application is related to our co-pending U.S. application Ser. No. 418,575, entitled CHEMICAL PROCESS, filed contemporaneously herewith on Sept. 15, 1982, directed to the preparation of esters of 3,5-dihydrocarbyl-4-hydroxybenzylmalonic acid by reacting an N,N-dihydrocarbyl-2,6-dihydrocarbyl-4-aminomethylphenol with an ester of a 1,3-dicarboxylic acid in the presence of an alkali or an alkaline earth metal hydride. This application also is related to our copending U.S. application Ser. No. 418,577, entitled CHEMICAL PROCESS, filed contemporaneously herewith on Sept. 15, 1982, directed to the preparation of esters of 3,5-dihydrocarbyl-4-hydroxybenzylmalonic acid by reacting a 2,6-dihydrocarbyl-4-hydroxymethylphenol with an ester of a 1,3-dicarboxylic acid in the presence of an alkali or an alkaline earth metal hydride.

TECHNICAL FIELD

This invention relates to 3,5-dihydrocarbyl-4-hydroxybenzylmalonic acid esters and the preparation and uses thereof as antioxidants for oxidizable organic materials when such materials are exposed to oxidative degradative conditions.

THE INVENTION

The materials of the invention are prepared by reacting a 2,6-dihydrocarbyl-4-halomethylphenol with an ester of a 1,3-dicarboxylic acid in the presence of an alkali or an alkaline earth metal hydride. Thus, in one embodiment of the invention there is provided a novel process for the preparation of 3,5-dihydrocarbyl-4-hydroxybenzylmalonic acid esters which comprises reacting a 2,6-dihydrocarbyl-4-halomethylphenol with an ester of a 1,3-dicarboxylic acid in the presence of an alkali or an alkaline earth metal hydride.

The process can be illustrated schematically by the following equations. Compounds having the general formula:

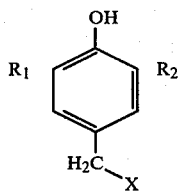
(I)

are reacted with compounds having the general formula:

(II)

in the presence of an alkali or an alkaline earth metal hydride to yield a benzylated malonic acid ester having the structural formula:

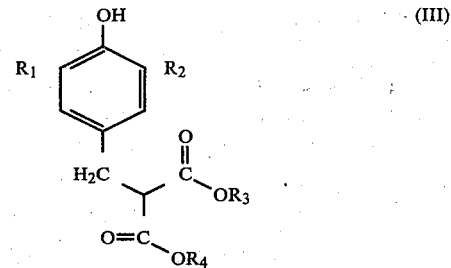
(III)

In the structural formulas above $R_1$ and $R_2$ are the same or different and are hydrogen or hydrocarbyl radicals, preferably alkyl, aralkyl or cycloalkyl radicals having up to at least 40 carbon atoms, and preferably from 3 to 8 atoms, at least one of which is branched on the alpha-carbon atom, with the provision that at least one of $R_1$ or $R_2$ must be other than hydrogen; $R_3$ and $R_4$ are the same or different and can be hydrogen, linear or branched alkyl radicals having up to at least 20 carbon atoms with the provision that at least one of $R_3$ or $R_4$ must be other than hydrogen and X is bromine, chlorine or iodine.

Thus, in another embodiment of the present invention there is provided a process for the preparation of 3,5-dihydrocarbyl-4-hydroxybenzylmalonic acid esters having the general formula:

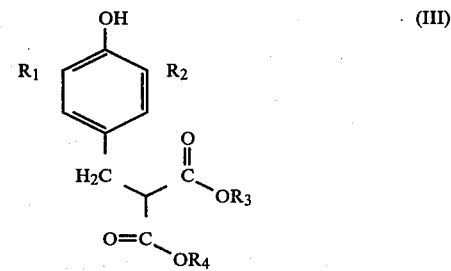
(III)

which comprises reacting a 2,6-dihydrocarbyl-4-halomethylphenol of the general formula:

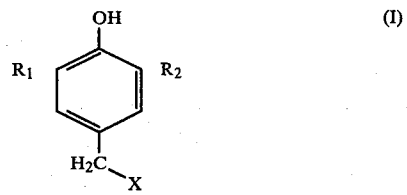
(I)

with an ester of a 1,3-dicarboxylic acid of the general formula:

in the presence of an alkali or an alkaline earth metal hydride wherein in the structural formulas above $R_1$ and $R_2$ are the same or different and are hydrogen or hydrocarbyl radicals having up to at least 40 carbon atoms with the provision that at least one of $R_1$ or $R_2$ must be other than hydrogen; $R_3$ and $R_4$ are the same or different and are hydrogen, linear or branched alkyl radicals having up to at least 20 carbon atoms with the provision that at least one of $R_3$ or $R_4$ must be other than hydrogen and X is chlorine, bromine or iodine.

Representative examples of radicals described above are secondary radicals such as secondary butyl, secondary amyl, secondary octyl; tertiary radicals such as tertiary butyl, tertiary hexyl and tertiary decyl; alkyl radicals such as methyl, ethyl, propyl, butyl, nonyl, decyl, tetradecyl, hexadecyl, nonadecyl; aralkyl radicals such as methyl phenyl and pentyl phenyl, and cycloalkyl radicals such as cyclopentyl, cyclohexyl and cycloheptyl radicals.

Representative examples of the Group I compounds are
  2,6-di-t-butyl-4-chloroethylphenol,
  2,6-di-t-butyl-4-bromomethylphenol,
  2,6-di-t-butyl-4-iodomethylphenol,
  2-methyl-6-isopropyl-4-chloromethylphenol,
  2-methyl-6-isopropyl-4-bromomethylphenol,
  2-methyl-6-isopropyl-4-iodomethylphenol,
  2-methyl-6-t-butyl-4-chloromethylphenol,
  2-methyl-6-t-butyl-4-bromomethylphenol,
  2-methyl-6-t-butyl-4-iodomethylphenol,
  2,6-diisopropyl-4-chloroethylphenol,
  2,6-diisopropyl-4-bromomethylphenol,
  2,6-diisopropyl-4-iodomethylphenol,
  2-sec-butyl-4-chloromethylphenol,
  2-sec-butyl-4-bromomethylphenol,
  2-sec-butyl-4-iodomethylphenol,
  2-isopropyl-4-chloromethylphenol,
  2-isopropyl-4-bromomethylphenol,
  2-isopropyl-4-iodomethylphenol,
  2-t-butyl-4-chloromethylphenol,
  2-t-butyl-4-bromomethylphenol,
  2-t-butyl-4-iodomethylphenol,
  2-ethyl-6-t-butyl-4-chloromethylphenol,
  2-ethyl-6-t-butyl-4-bromomethylphenol,
  2-ethyl-6-t-butyl-4-iodomethylphenol,
  2,6-diheptyl-4-chloromethylphenol,
  2,6-diheptyl-4-bromomethylphenol,
  2,6-diheptyl-4-iodomethylphenol,
  2-ethyl-6-methyl-4-chloromethylphenol,
  2-ethyl-6-methyl-4-bromomethylphenol,
  2-ethyl-6-methyl-4-iodomethylphenol,
  2-t-butyl-6-heptyl-4-chloromethylphenol,
  2-t-butyl-6-heptyl-4-bromomethylphenol,
  2-t-butyl-6-heptyl-4-iodomethylphenol,
  2-methyl-6-ethyl-4-chloromethylphenol,
  2-methyl-6-ethyl-4-bromomethylphenol,
  2-methyl-6-ethyl-4-iodomethylphenol, and the like.

Representative examples of Group II esters of 1,3-dicarboxylic acid compounds are
  malonic acid, dimethyl ester,
  malonic acid, diethyl ester,
  malonic acid, diisopropyl ester,
  malonic acid, di-n-hexyl ester,
  malonic acid, dioctyl ester,
  malonic acid, didodecyl ester,
  malonic acid, ethyl, methyl diester,
  malonic acid, ethyl, isopropyl diester,
  malonic acid, n-butyl, ethyl diester,
  malonic acid, n-butyl, dodecyl diester,
  malonic acid, octyl, ethyl diester,
  malonic acid, ethyl monoester,
  malonic acid, n-propyl monoester,
  malonic acid, n-butyl monoester,
  malonic acid, n-hexyl monoester,
  malonic acid, octyl monoester,
  malonic acid, dodecyl monoester, and the like.

Representative examples of Group III benzylated malonic acid esters functioning as antioxidants, are
  3,5-di-t-butyl-4-hydroxybenzylmalonic acid, dimethyl ester,
  3,5-di-t-butyl-4-hydroxybenzylmalonic acid, diethyl ester,
  3,5-di-t-butyl-4-hydroxybenzylmalonic acid, diisopropyl ester,
  3,5-di-t-butyl-4-hydroxybenzylmalonic acid, di-n-hexyl ester,
  3,5-di-t-butyl-4-hydroxybenzylmalonic acid, dioctyl ester,
  3,5-di-t-butyl-4-hydroxybenzylmalonic acid, didodecyl ester,
  3,5-di-t-butyl-4-hydroxybenzylmalonic acid, ethyl, methyl diester,
  3,5-di-t-butyl-4-hydroxybenzylmalonic acid, ethyl, isopropyl diester,
  3,5-di-t-butyl-4-hydroxybenzylmalonic acid, n-butyl, ethyl diester,
  3,5-di-t-butyl-4-hydroxybenzylmalonic acid, n-butyl, dodecyl diester,
  3,5-di-t-butyl-4-hydroxybenzylmalonic acid, octyl, methyl diester,
  3,5-di-t-butyl-4-hydroxybenzylmalonic acid, octyl, ethyl diester,
  3,5-di-t-butyl-4-hydroxybenzylmalonic acid, ethyl monoester,
  3,5-di-t-butyl-4-hydroxybenzylmalonic acid, n-propyl monoester,
  3,5-di-t-butyl-4-hydroxybenzylmalonic acid, n-butyl monoester,
  3,5-di-t-butyl-4-hydroxybenzylmalonic acid, n-hexyl monoester,
  3,5-di-t-butyl-4-hydroxybenzylmalonic acid, octyl monoester,
  3,5-di-t-butyl-4-hydroxybenzylmalonic acid, dodecyl monoester,
  3-ethyl-5-ethyl-4-hydroxybenzylmalonic acid, dioctyl ester,
  3-n-butyl-5-octyl-4-hydroxybenzylmalonic acid, ethyl, methyl diester,
  3-ethyl-5-methyl-4-hydroxybenzylmalonic acid, ethyl monoester,
  3,5-dioctyl-4-hydroxybenzylmalonic acid, octyl monoester, and the like.

In general, any of the alkali or alkaline earth metal hydrides may be used in the practice of the present process. These include sodium hydride, potassium hydride, lithium hydride, magnesium hydride, calcium hydride, and the like. Sodium hydride is preferred.

The process of the invention is carried out by reacting the halomethylphenol starting material with at least 1 molar equivalent of malonic acid ester reactant although an excess of ester reactant can be used. A preferred range of malonic acid ester reactant to halomethylphenol reactant is from about 1 to 10 moles of ester per mole of halomethylphenol.

At least 1 mole of hydride per mole of halomethylphenol reactant should be used in the process of the invention, although an amount of hydride up to about 50 moles of hydride per mole of halomethylphenol reactant can be used, if desired.

The reaction is advantageously conducted at a temperature of from about 50° C. to about 500° C. While lower temperatures can be used, the reaction rates are generally correspondingly lower. Temperatures above 500° C. can be used, but excessive decomposition of the reaction components can occur. Reflux temperature at atmospheric pressure is effective and preferred.

Typically, the reaction can be conducted at atmospheric pressure. However, higher pressures up to about 1000 psig may be used, if desired.

The use of a solvent for the reaction mixture is not generally required, especially if an excess of malonic acid ester reactant is used. However, if desired, a solvent which is inert under the reaction conditions, i.e., those solvents which do not enter into the reaction, may be added to the reaction vessel. Useful solvents comprise aprotic solvents which include ethers such as diethyl ether, dibutyl ether, 1-ethoxyhexane, tetrahydrofuran, 1,4-dioxane, 1,3-dioxolane, diglyme, 1,2-diethoxyethane, and tertiary amines such as pyridine, N-ethylpiperidine, triethylamine, tributylamine, N,N-diphenyl-N-methylamine, N,N-dimethylalanine, etc. Especially useful solvents are dipolar aprotic solvents such as dimethyl sulfoxide, N,N-dimethylformamide, N,N-dimethylacetamide, dimethyl sulfone, tetramethylene sulfone, N-methylpyrrolidinone, acetonitrile and like materials. Other solvents which are inert under the reaction conditions may be used: for example, low boiling hydrocarbons, halogenated hydrocarbons, examples of which are benzene, toluene, tetrachloroethane, the chlorinated benzenes, the chlorinated toluenes, etc., and lower alkanols having up to about 6 carbon atoms. These include methanol, ethanol, n-propanol, isopropyl alcohol, n-butanol, sec-butyl alcohol, t-butyl alcohol, n-pentanol, isopentyl alcohol, n-hexanol and isohexyl alcohol.

The amount of solvent can be expressed as a volume ratio of solvent to halomethylphenol reactant. Suitable volume ratios of solvent to halomethylphenol reactant can be from about 0/1 to about 500/1 and preferably from about 1/1 to about 300/1.

The mode of addition in the process is not particularly critical. Accordingly, it is convenient to add the halomethylphenol reactant to a mixture of the other materials, add the malonic acid ester compound to a mixture of the other materials, add the reactants to a mixture of the halomethylphenol and solvent, introduce all ingredients simultaneously into the reaction zone, or the like.

The process should be carried out for the time sufficient to convert substantially all of the halomethylphenol reactant to the corresponding benzylated malonic acid ester. The length of time for optimum yield will depend primarily upon the reaction temperature and the particular solvent, if any, used in the reaction. In general, excellent yields of the benzylated malonic acid ester are obtained in from about two to twenty-four hours.

Although not required, the process can be conducted in a substantially anhydrous reaction system, and accordingly, the components of the reaction system are brought together and maintained under a substantially dry, inert atmosphere. By "substantially anhydrous" is meant a reaction system wherein the total amount of water present is no more than about 5 percent by weight, based on the reaction mixture. When the amount of water in the system exceeds this, both reaction rate and yield of product decrease.

The process may readily be conducted in a batchwise, semi-batch or continuous manner and in conventional equipment.

The process of the invention when run continously can be illustrated schematically by the equation shown below. $R_1$, $R_2$, $R_3$ and $R_4$ are the same radicals as described and exemplified above.

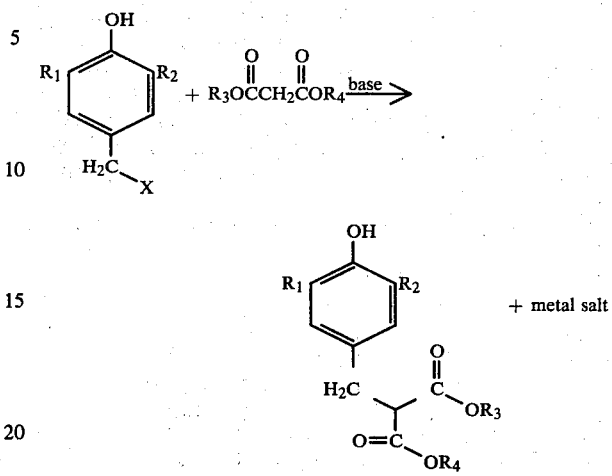

Under the reaction conditions, elimination of halide occurs yielding a quinone methide intermediate which undergoes nucleophilic attack by the malonic acid ester reactant to form the desired benzylated malonic acid ester product. Some bis(hydroxyphenyl)methane by-product may be formed.

The benzylated malonic acid ester product is easily separated from the reaction mixture by such means as distillation, extraction, crystallization and other methods obvious to those skilled in the chemical processing art.

The benzylated malonic acid ester products prepared by the process of this invention have antioxidant properties and are capable of stabilizing polymers normally subject to oxidative degradation when incorporated into the polymers using conventional techniques such as by addition to polymer lattices; or by addition to solid polymers on a mill or in a Banbury. Further, the novel compounds of this invention are effective antioxidants in both unleaded and leaded gasolines made from a wide variety of base stocks and for engine and industrial oils which are derived from crude petroleum or produced synthetically.

The practice of this invention will be still further apparent by the following illustrative example.

EXAMPLE I

A dimethylformamide solution (25 mmols) of diethyl sodiomalonate (generated by treating a dimethylformamide solution of 2.4 g; 15 mmols diethyl malonate with 0.72 g; 30 mmols oil-free sodium hydride) was added with stirring under a nitrogen atmosphere to a dimethylformamide solution (25 mLs) of 2,6-di-t-butyl-4-chloromethylphenol (2.49 g; 10 mmols). The reaction mixture was heated to a temperature of 125° C. and held at that temperature for 3 hours and then poured into cold 2N hydrochloric acid (100 mLs). The aqueous reaction slurry was extracted with diethyl ether (3×30 mLs). The combined organic extract was dried (MgSO$_4$) and concentrated to give 2.44 g; 39% by VPC of 3,5-di-t-butyl-4-hydroxybenzylmalonic acid, diethyl ester.

Having disclosed the process of the present invention, one skilled in the art can readily envision various modifications and changes which are nevertheless within the scope of the invention. Therefore, it is desired that the process of this invention be limited only by the lawful scope of the appended claims.

We claim:

1. A process for the preparation of 3,5-di-hydrocarbyl-4-hydroxybenzylmalonic acid esters corresponding to the formula:

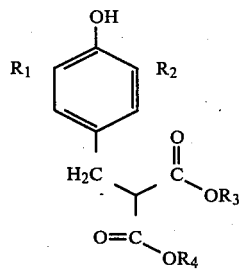

which comprises reacting one molar equivalent of a 2,6-dihydrocarbyl-4-halomethylphenol corresponding to the formula:

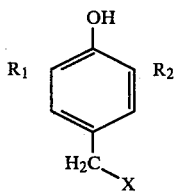

with at least one molar equivalent of an ester of a 1,3-dicarboxylic acid corresponding to the formula:

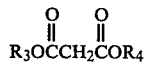

in the presence of at least one molar equivalent of an alkali metal hydride or an alkaline earth metal hydride wherein $R_1$ and $R_2$ are the same or different and are hydrogen or hydrocarbyl radicals having up to at least 40 carbon atoms with the provision that at least one of $R_1$ or $R_2$ must be other than hydrogen, $R_3$ and $R_4$ are the same or different and are hydrogen, linear or branched alkyl radicals having up to at least 20 carbon atoms with the provision that at least one of $R_3$ or $R_4$ must be other than hydrogen and X is chlorine, bromine or iodine.

2. The process of claim 1 wherein compounds having the structural formula (I) are selected from the group consisting of
   2,6-di-t-butyl-4-chloroethylphenol,
   2,6-di-t-butyl-4-bromomethylphenol,
   2,6-di-t-butyl-4-iodomethylphenol,
   2-methyl-6-isopropyl-4-chloromethylphenol,
   2-methyl-6-isopropyl-4-bromomethylphenol,
   2-methyl-6-isopropyl-4-iodomethylphenol,
   2-methyl-6-t-butyl-4-chloromethylphenol,
   2-methyl-6-t-butyl-4-bromomethylphenol,
   2-methyl-6-t-butyl-4-iodomethylphenol,
   2,6-diisopropyl-4-chloroethylphenol,
   2,6-diisopropyl-4-bromomethylphenol,
   2,6-diisopropyl-4-iodomethylphenol,
   2-sec-butyl-4-chloromethylphenol,
   2-sec-butyl-4-bromomethylphenol,
   2-sec-butyl-4-iodomethylphenol,
   2-isopropyl-4-chloromethylphenol,
   2-isopropyl-4-bromomethylphenol,
   b 2-isopropyl-4-iodomethylphenol,
   2-t-butyl-4-chloromethylphenol,
   2-t-butyl-4-bromomethylphenol,
   2-t-butyl-4-iodomethylphenol,
   2-ethyl-6-t-butyl-4-chloromethylphenol,
   2-ethyl-6-t-butyl-4-bromomethylphenol,
   2-ethyl-6-t-butyl-4-iodomethylphenol,
   2,6-diheptyl-4-chloromethylphenol,
   2,6-diheptyl-4-bromomethylphenol,
   2,6-diheptyl-4-iodomethylphenol,
   2-ethyl-6-methyl-4-chloromethylphenol,
   2-ethyl-6-methyl-4-bromomethylphenol,
   2-ethyl-6-methyl-4-iodomethylphenol,
   2-t-butyl-6-heptyl-4-chloromethylphenol,
   2-t-butyl-6-heptyl-4-bromomethylphenol,
   2-t-butyl-6-heptyl-4-iodomethylphenol,
   2-methyl-6-ethyl-4-chloromethylphenol,
   2-methyl-6-ethyl-4-bromomethylphenol, and
   2-methyl-6-ethyl-4-iodomethylphenol.

3. The process of claim 1 wherein compounds having the structural formula (II) are selected from the group consisting of
   malonic acid, dimethyl ester,
   malonic acid, diethyl ester,
   malonic acid, diisopropyl ester,
   malonic acid, di-n-hexyl ester,
   malonic acid, dioctyl ester,
   malonic acid, didodecyl ester,
   malonic acid, ethyl, methyl diester,
   malonic acid, ethyl, isopropyl diester,
   malonic acid, n-butyl, ethyl diester,
   malonic acid, n-butyl, dodecyl diester,
   malonic acid, octyl, ethyl diester,
   malonic acid, ethyl monoester,
   malonic acid, n-propyl monoester,
   malonic acid, n-butyl monoester,
   malonic acid, n-hexyl monoester,
   malonic acid, octyl monoester, and
   malonic acid, dodecyl monoester.

4. The process of claim 1 wherein said alkali metal hydride or alkaline earth metal hydride is selected from the group consisting of sodium hydride, barium hydride, lithium hydride, magnesium hydride and calcium hydride.

5. The process of claim 1 wherein the compounds produced are selected from the group consisting of
   3,5-di-t-butyl-4-hydroxybenzylmalonic acid, dimethyl ester,
   3,5-di-t-butyl-4-hydroxybenzylmalonic acid, diethyl ester,
   3,5-di-t-butyl-4-hydroxybenzylmalonic acid, diisopropyl ester,
   3,5-di-t-butyl-4-hydroxybenzylmalonic acid, di-n-hexyl ester,
   3,5-di-t-butyl-4-hydroxybenzylmalonic acid, dioctyl ester,
   3,5-di-t-butyl-4-hydroxybenzylmalonic acid, didodecyl ester,
   3,5-di-t-butyl-4-hydroxybenzylmalonic acid, ethyl, methyl diester,
   3,5-di-t-butyl-4-hydroxybenzylmalonic acid, ethyl, isopropyl diester,
   3,5-di-t-butyl-4-hydroxybenzylmalonic acid, n-butyl, ethyl diester,
   3,5-di-t-butyl-4-hydroxybenzylmalonic acid, n-butyl, dodecyl diester, 3,5-di-t-butyl-4-hydroxybenzylmalonic acid, octyl, methyl diester,
3,5-di-t-butyl-4-hydroxybenzylmalonic acid, octyl, ethyl diester,
3,5-di-t-butyl-4-hydroxybenzylmalonic acid, ethyl monoester,
3,5-di-t-butyl-4-hydroxybenzylmalonic acid, n-propyl monoester,
3,5-di-t-butyl-4-hydroxybenzylmalonic acid, n-butyl monoester,
3,5-di-t-butyl-4-hydroxybenzylmalonic acid, n-hexyl monoester,
3,5-di-t-butyl-4-hydroxybenzylmalonic acid, octyl monoester,
3,5-di-t-butyl-4-hydroxybenzylmalonic acid, dodecyl monoester,
3-ethyl-5-ethyl-4-hydroxybenzylmalonic acid, dioctyl ester,
3-n-butyl-5-octyl-4-hydroxybenzylmalonic acid, ethyl, methyl diester,
3-ethyl-5-methyl-4-hydroxybenzylmalonic acid, ethyl monoester, and
3,5-dioctyl-4-hydroxybenzylmalonic acid, octyl monoester.

6. The process of claim 1 wherein the molar ratio of malonic acid ester reactant to halomethylphenol reactant is from about 1-10 moles of malonic acid ester per mole of halomethylphenol.

7. The process of claim 1 wherein said reaction is conducted at elevated temperature.

8. The process of claim 7 wherein said reaction is carried out at a temperature of from about 50° C. to about 500° C.

9. The process of claim 1 wherein said reaction is carried out under pressure in the range of from about atmospheric up to about 1000 psig.

10. The process of claim 1 wherein said reaction is carried out at temperature in the range of about 50° C. to about 500° C. and under pressure in the range of about atmospheric to about 1000 psig.

11. The process of claim 1 wherein said reaction is carried out in the presence of a solvent which is inert under the reaction conditions.

12. The process of claim 11 wherein the said solvent is an aprotic solvent.

13. The process of claim 11 wherein said aprotic solvent is a dipolar aprotic solvent.

14. The process of claim 13 wherein said dipolar aprotic solvent is selected from dimethyl sulfoxide, N,N-dimethylformamide, N,N-dimethylacetamide, dimethyl sulfone, tetramethylene sulfone, N-methylpyrrolidinone and acetonitrile.

15. The process of claim 11 wherein said solvent is selected from the group consisting of low boiling hydrocarbons, halogenated hydrocarbons and lower alkanols having from 1 to about 6 carbon atoms.

16. The process of claim 11 wherein the volume ratio of solvent to halomethylphenol reactant is from about 0/1 to about 500/1.

17. The process of claim 1 wherein the reaction is carried out under a substantially dry inert atmosphere.

* * * * *